United States Patent
Kennedy et al.

(10) Patent No.: US 7,628,075 B2
(45) Date of Patent: Dec. 8, 2009

(54) MULTIPLE-FREQUENCY ULTRASONIC TEST PROBE, INSPECTION SYSTEM, AND INSPECTION METHOD

(75) Inventors: James C. Kennedy, Kent, WA (US); Barry A. Fetzer, Renton, WA (US); Jeffry J. Garvey, DeMotte, IN (US); Mark L. Little, Auburn, WA (US)

(73) Assignee: The Boeing Company, Chicago, IL (US)

( * ) Notice: Subject to any disclaimer, the term of this patent is extended or adjusted under 35 U.S.C. 154(b) by 299 days.

(21) Appl. No.: 11/759,105

(22) Filed: Jun. 6, 2007

(65) Prior Publication Data

US 2007/0227250 A1    Oct. 4, 2007

Related U.S. Application Data

(63) Continuation-in-part of application No. 11/178,637, filed on Jul. 11, 2005, now Pat. No. 7,337,673.

(51) Int. Cl.
*G01N 29/24* (2006.01)
*G01N 29/28* (2006.01)

(52) U.S. Cl. .......................................... 73/628; 73/644
(58) Field of Classification Search ................... 73/644, 73/628
See application file for complete search history.

(56) References Cited

U.S. PATENT DOCUMENTS

| | | | | |
|---|---|---|---|---|
| 2,992,553 A | * | 7/1961 | Joy | 73/636 |
| 3,898,840 A | * | 8/1975 | McElroy | 73/644 |
| 3,958,451 A | * | 5/1976 | Richardson | 73/644 |
| 4,413,520 A | * | 11/1983 | Murakami et al. | 73/609 |
| 4,817,615 A | * | 4/1989 | Fukukita et al. | 600/438 |
| 5,635,644 A | * | 6/1997 | Ishikawa et al. | 73/614 |
| 5,814,731 A | * | 9/1998 | Alexander et al. | 73/644 |
| 5,942,687 A | * | 8/1999 | Simmonds et al. | 73/579 |
| 6,312,383 B1 | * | 11/2001 | Lizzi et al. | 600/437 |
| 6,537,224 B2 | * | 3/2003 | Mauchamp et al. | 600/459 |
| 6,722,202 B1 | | 4/2004 | Kennedy et al. | |
| 2006/0010980 A9 | | 1/2006 | Bossi et al. | |
| 2006/0053892 A1 | | 3/2006 | Georgeson et al. | |
| 2006/0055399 A1 | | 3/2006 | Georgeson et al. | |
| 2007/0006658 A1 | | 1/2007 | Kennedy et al. | |
| 2007/0035204 A1 | * | 2/2007 | Angelsen et al. | 310/311 |
| 2007/0044562 A1 | * | 3/2007 | Sarr | 73/618 |

* cited by examiner

*Primary Examiner*—David A. Rogers
*Assistant Examiner*—Rose M Miller
(74) *Attorney, Agent, or Firm*—Yee & Associates, P.C.; Dennis R. Plank

(57) ABSTRACT

Improved apparatus, systems, and methods for inspecting a structure are provided that use a probe having two ultrasonic transducer arrays. This enables simultaneous testing using two different test frequencies. The probe uses pulse echo ultrasonic signals at different frequencies to inspect the structure. The probe includes a support body having a fluid conduit formed therein. The fluid conduit provides flow paths for a couplant (such as water) that is used to couple the ultrasonic signals between the structure under test and the arrays. The fluid conduit is configured to quickly eject couplant and bubbles contained in the couplant.

21 Claims, 13 Drawing Sheets

MULTIPLE-FREQUENCY ULTRASONIC TEST PROBE, INSPECTION SYSTEM, AND INSPECTION METHOD

CROSS-REFERENCE TO RELATED APPLICATION

This application is a continuation-in-part of U.S. patent application Ser. No. 11/178,637, filed Jul. 11, 2005 and published as U.S. patent application publication No. 2007/0006657 A1, which is incorporated herein by reference.

TECHNICAL FIELD

Embodiments of the subject matter described herein relate generally to an apparatus, system, and method for inspecting a structure and, more particularly, to an apparatus, system, and method for non-destructive pulse echo ultrasonic inspection of a structure using multiple test frequencies.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, dictate that devices and processes are available to ensure structural integrity, production quality, and life-cycle support for safe and reliable use. As such, it is frequently desirable to inspect such structures to identify characteristics such as discontinuities, voids, or porosity of the structures.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar characteristics and porosity, and/or to identify other features in the structure. Resonance, PE or mechanical impedance sensors are typically used to provide indications of voids or porosity, such as in adhesive bondlines of the structure. High resolution inspection of aircraft structure is commonly performed using semi-automated ultrasonic testing (UT) to provide a plan view image of the part or structure under inspection. While solid laminates and some composite structures are commonly inspected using one-sided pulse echo ultrasonic (PEU) testing, composite sandwich structures are commonly inspected using through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and/or detectors. As such, the inspection of the structure can proceed more rapidly and efficiently, thereby reducing the costs associated with the inspection. However, it has traditionally not always been possible to perform continuous scanning of a structure with holes and off the edges of the structure. For example, inspection probes which contact and ride along the surface of the structure under inspection and are typically supported against the structure by the pull of gravity or by pressure exerted by a motion control system, referred to as part-riding probes, may fall through a hole in a structure or off the edge of the structure. Although a structure can be inspected in a manner to scan around holes, a second inspection method typically must be performed for inspecting the edges of the structure and edges defining holes in the structure. For example, a technician can manually scan around the edges of the structure and the edges of holes in a structure using a pulse-echo or through transmission ultrasonic hand probe.

Non-destructive inspection may be performed manually by technicians who typically move an appropriate sensor over the structure. Manual scanning requires a trained technician to move the sensor over all portions of the structure needing inspection. While manual scanning may be required around the edges of the structure and the edges of holes in a structure, manual scanning may also be employed for scanning the remainder of the structure.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For single sided inspection methods, such as pulse echo ultrasonic inspection, a single-arm robotic device, such as an R-2000iA™ series six-axis robot from FANUC Robotics of Rochester Hills, Mich., or an IRB 6600 robot from ABB Ltd. of Zurich, Switzerland, may be used to position and move a pulse-echo ultrasonic inspection device. For through transmission inspection, a device such as the Automated Ultrasonic Scanning System (AUSS®) system may be used. The AUSS system has two robotically controlled probe arms that can be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure for through transmission inspection which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. The AUSS system can also perform pulse echo inspections, and simultaneous dual frequency inspections.

Many structures, however, incorporate holes through which a part-riding probe may fall through and edges over which a part-riding probe may fall off. Further, most structures require inspection of edges around the structure and defining holes in the structure. Accordingly, improved apparatus, systems, and methods for inspecting structures with holes and inspecting structures at edges are desired.

Conventional ultrasonic probes used to test structures employ ultrasonic transducers (or a transducer array module) that are configured to test at only one ultrasonic frequency. The particular frequency used may be selected according to the particular characteristic of interest, such as porosity. Consequently, if it is necessary to test for different ranges of the characteristic of interest (e.g., high porosity and low porosity), then the probe must be passed over the structure multiple times. For example, the probe might be used to scan the entire structure using a first test frequency, then subsequently used to scan the entire structure using a second test frequency. Multiple-pass testing in this manner is inefficient and adds cost to the testing process.

Some existing ultrasonic probes used to test structures employ a fluid that serves as a couplant between the ultrasonic transducers and the structure under test. The couplant is typically a liquid such as water. During operation, bubbles may appear in the flow chamber or flow path of the couplant, and the presence of bubbles near the ultrasonic transducers may lead to inaccurate test data. Due to the need to collect ultrasonic data quickly and accurately, any air bubbles should be cleared from the ultrasonic transducers within a very short period of time (within a few seconds).

BRIEF SUMMARY

The subject matter described herein relates to an improved apparatus, systems, and methods for inspecting a structure using an inspection probe that includes sled-like appendages, referred to herein as sled appendages or sleds, an axial braking system and a probe extension braking system. Embodiments of the inspection probes described herein may be used in conjunction with a motion control system that both moves the probe over the structure for inspection and operates with the axial and extension braking systems for when the probe travels over holes or off edges of the structure. An inspection probe may also be used with an extension coupling device between the motion control system and the probe to press the probe against the structure for adjusting to changes in surface contours of the structure, rather than requiring the motion control system to make detailed changes in orientation and movement of the probe to adjust to changes in surface contours. Either the motion control system or a separate device, such as an extension coupling device, would be used to press the inspection probe against the structure so the inspection probe will ride across the structure on the sled appendages.

Embodiments of the system combine the physical structure of the sled appendages with the axial braking system to fix the position of the sled appendages for traveling over holes or off an edge of the structure, including large holes or cut-outs in the structure which are also referred to herein as holes. Embodiments of the system can be used for various inspection applications but are particularly useful for inspection of structures that include holes and require inspection of the edges around the structure or defining a hole or have contoured surfaces. A probe will include one or more sensors, typically pulse echo ultrasonic transducers, possibly defining an array of pulse echo ultrasonic transducers. Such devices can be used for high resolution defect detection in structures of varying shapes and sizes. Embodiments of apparatus, systems, and methods described herein can be used for inspection of structures during manufacture or in-service. Further, embodiments described herein provide new inspection capabilities for non-destructive inspection of large and small structures, particularly including the edges of structures and structures with holes.

Embodiments of apparatus, systems, and methods described herein typically operate in array modes using an array of pulse echo ultrasonic transducers, thereby increasing inspection speed and efficiency while reducing cost. Such apparatus, systems, and methods are also capable of operating with a single or a plurality of pulse echo ultrasonic transducers.

For continuous scanning applications, the embodiments of apparatus, systems, and methods permit the probe to contact and ride along the surface of the structure using one or more sled appendages, thereby reducing the necessary sophistication of a motion control system that is typically required by conventional scanning systems to maintain the probe in a predefined orientation and predefined position with respect to the surface of the structure. By allowing the probe to ride across the structure, the motion control system, or a separate device such as an extension coupler, only needs to press the probe against the structure, but does not need to know the surface contours of the structure because the act of pressing the probe against the surface combined with the sled appendages having freedom of motion and the axial motion of the probe compensate for surface contours. In addition to sled appendages, the probe may also use contact members to support the probes against the respective surfaces of the structure, such as roller bearings along the bottom of the sled appendages. The sled appendages are rotatably connected to permit freedom of motion of the sled appendages for riding along contoured surfaces. Contact with the surface ensures consistent orientation of transducers with respect to the structure for pulse echo ultrasonic inspection. Contact with the surface also permits accurate position measurement of the inspection device during continuous scanning, such as keeping an optical or positional encoder in physical and/or visual contact with the surface of the structure under inspection. Contact with the surface also permits the probe to disperse a couplant between the surface of the structure and the pulse echo ultrasonic transducers. Where a couplant is used, a probe may also include a bubbler shoe that disperses the couplant around each pulse echo ultrasonic transducer to independently couple the signal from each transducer to the surface of the part. By individually coupling each transducer to the surface of the part, the bubbler shoe compensates for when the probe travels over a hole or off an edge of the structure where all of the transducers are not over the surface of the structure. In such a manner, only the probes over the hole or off the edge of the structure will lose the coupling with the surface, but the transducers remaining over the surface of the structure will continue to be independently coupled.

The axial and extension braking systems of a probe are used to fix the position of the sled appendages for traveling over holes or off an edge of the structure. Thus, for continuous scanning applications, the probe contacts and rides along the surface of the structure on the sled appendages, but as the probe approaches a hole or edge, the axial and extension braking systems, either using data of the hole and edge positions for the structure and the current location of the probe or using braking signals from a motion control system, fixes the current position of the sled appendages for traveling over the hole or off an edge and again contacting and riding along the surface of the structure after passing the hole or retracting from the edge at which time the axial braking system releases to permit the sled appendages to follow the contour of the surface of the structure. An axial braking system of an embodiment of a probe can operate in more than one axis, and typically operates in two perpendicular axes referred to herein as the x-axis perpendicular to the distal length of the sled appendages to control the front-to-back tilt, or pitch, of the sled appendages and the y-axis parallel to the distal length of the sled appendages to control the side-to-side slant, or roll, of the sled appendages.

According to one embodiment, an apparatus, system, and method for non-destructive inspection of a structure employs a probe which is configured for traveling over a surface of the structure along sled appendages and using an axial braking system for traveling over holes and off edges of the structure. The probe includes at least one pulse echo ultrasonic transducer. A plurality of pulse echo ultrasonic transducers may be arranged in an array for faster and more complete scanning of the structure. If a couplant is used to couple the transducers to the surface of the structure, the probe may include a bubbler shoe to individually couple each transducer to the surface of the structure to prevent loss of coupling of transducers remaining over the surface of the structure when one or more transducers are over a hole or off an edge. The probe may also include a visual inspection sensor for providing position or optical information related to the location of the probe or transducers thereof.

An embodiment of a method may involve: providing a probe with at least one pulse echo ultrasonic transducer, at least one sled appendage for contacting a surface of a structure, and axial and extension braking systems; transmitting pulse echo ultrasonic signals from the transducer into the structure; receiving pulse echo ultrasonic signals at the transducer from the structure; and fixing the position of the sled for scanning a portion of the structure where only a portion of the probe is over the surface of the structure.

An alternate embodiment of an apparatus for non-destructive inspection of a structure includes a support body, a first ultrasonic transducer array coupled to the support body and configured to inspect the structure at a first frequency as the support body is moved over the structure, a second ultrasonic transducer array coupled to the support body and configured to inspect the structure at a second frequency as the support body is moved over the structure, and a fluid conduit formed within the support body and configured to transport a couplant for the first ultrasonic transducer array and the second ultrasonic transducer array.

Another alternate embodiment of an apparatus for non-destructive inspection of a structure includes a support body having formed therein a fluid inlet and a fluid conduit in communication with the fluid inlet, and an ultrasonic transducer array coupled to the support body and configured to inspect the structure as the support body is moved over the structure. The ultrasonic transducer array has a first end, a second end, and a plurality of transducers arranged between the first end and the second end. The fluid conduit is configured to promote flow of a couplant from the fluid inlet, to a location proximate the first end of the ultrasonic transducer array, across the ultrasonic transducer array, and to a location proximate the second end of the ultrasonic transducer array.

An alternate system for inspecting a structure includes a motion control system, a probe coupled to and moved by the motion control system over the structure, and data collection equipment coupled to the probe. The probe includes a support body, a plurality of ultrasonic transducer arrays held by the support body and configured to simultaneously inspect the structure using a plurality of frequencies as the probe is moved over the structure, and a fluid conduit formed within the support body and configured to provide a couplant to the plurality of ultrasonic transducer arrays. The data collection equipment is coupled to the plurality of ultrasonic transducer arrays and the equipment is configured to simultaneously receive, from the plurality of ultrasonic transducer arrays, test signals corresponding to the plurality of frequencies.

Another embodiment of a method for inspecting a structure involves: holding a probe against a surface of the structure, the probe comprising a high frequency ultrasonic transducer array, a low frequency ultrasonic transducer array, and a fluid conduit configured to transport a couplant to the high frequency ultrasonic transducer array and the low frequency ultrasonic transducer array; simultaneously transmitting high frequency ultrasonic signals to the high frequency ultrasonic transducer array and low frequency ultrasonic signals to the low frequency ultrasonic transducer array; coupling ultrasonic signals between the high frequency ultrasonic transducer array and the structure using the couplant; coupling ultrasonic signals between the low frequency ultrasonic transducer array and the structure using the couplant; moving the probe across the surface of the structure; and processing a first set of detection signals from the high frequency ultrasonic transducer array and a second set of detection signals from the low frequency ultrasonic transducer array, the first set of detection signals being generated in response to transmitted high frequency ultrasonic signals, and the second set of detection signals being generated in response to transmitted low frequency ultrasonic signals.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
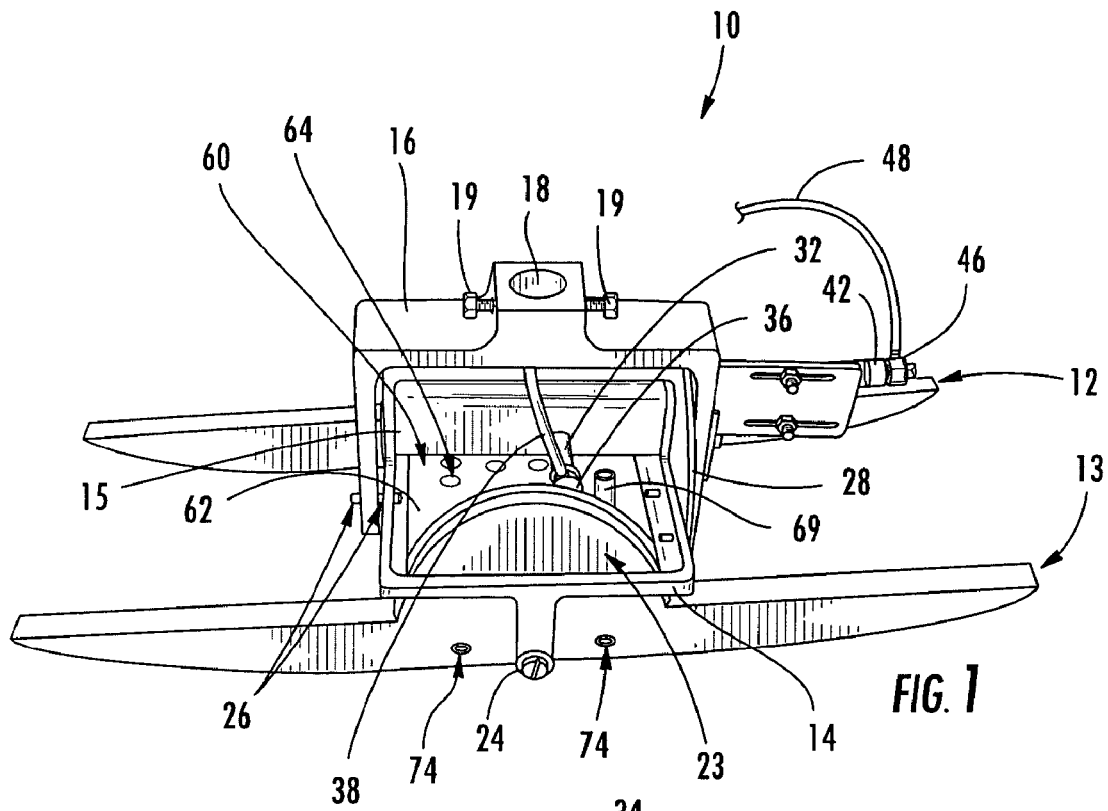
FIG. 1 is a schematic diagram of an embodiment of an inspection apparatus.

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description. For the sake of brevity, conventional aspects of pulse-echo ultrasonic transducers, nondestructive testing procedures, robotics, and other aspects of the systems (and the individual operating components of the systems) may not be described in detail herein.

The contents of U.S. Pat. No. 6,722,202 (titled "Method and Apparatus for Inspecting a Structure Utilizing Magnetically Attracted Probes"), U.S. patent application publication No. 2006/0010980 A9 (titled "Non-Destructive Inspection Device for Inspecting Limited-Access Features of a Structure"), U.S. patent application publication No. 2006/0055399 A1 (titled "Magnetically Attracted Inspecting Apparatus and Method Using a Ball Bearing"), U.S. patent application publication No. 2006/0053892 A1 (titled "Magnetically Attracted Inspecting Apparatus and Method Using a Fluid Bearing"), and U.S. patent application publication No. 2007/0006658 A1 (titled "Ultrasonic Inspection Apparatus, System, and Method") are incorporated herein by reference.

The term "holes" refers to holes of varying sizes in a structure, including features described as "cut-outs" in the structure. The term "edges" refers generally to the sides of the structure, but also includes reference to the perimeter of holes, particularly large holes or cut-outs through which a conventional part-riding probe might fall through. Thus, holes may be described as having edges, and the term edges is inclusive of both an external perimeter of a structure and perimeters of internal holes in the structure. Although being characteristically different, as used herein holes and edges differ primarily by the manner in which an embodiment of a probe operates near these features. For example, the probe typically travels over a hole or cut-out but travels off an edge of the structure, and possibly returning over the structure from an edge. Further, while in some instances in the description below using only one of the two terms holes and edges may be sufficient, typically both terms are used to emphasize that the described function or operation applies to both holes in the structure and edges of the structure, and not merely one of these features.

The term "rotatably" refers to a characteristic of angular motion in at least one plane, and typically only one plane as may be defined by a connection about an axis-line as described in the examples below. However, a rotatable connection may also be defined by a connection that provides angular motion in more than one plane, such as a ball-and-socket joint connection that permits motion of the joint without permitting rotation in at least one plane, such as to provide freedom of motion to pitch and roll, but not yaw.

The embodiments described here relate to apparatus and methods for an ultrasonic array probe for inspecting a structure while riding on a surface of the structure. The probe has the ability to travel over holes and off edges of the structure during inspection. Typically a probe would be moved over a structure by a motion control system, such as an R-2000iA™ series six-axis robot from FANUC Robotics, an IRB 6600 robot from ABB, or similar automated robotic motion control system, and possibly also using an extension coupler to compensate for surface contours rather than requiring the motion control system to compensate for surface contours. An example motion control system with an extension coupler for manipulating an inspection apparatus suitable for use with the embodiments mentioned herein is described in U.S. patent application publication No. 2007/0006658 A1, entitled "Ultrasonic Inspection Apparatus, System, and Method," which is incorporated herein by reference. The combination of sled appendages and an axial braking system provide the configuration for the probe to be able to travel over holes and off edges of the structure during inspection. By comparison, conventional part-riding probes, probes which contact and ride along the surface of the structure under inspection, may fall through a large hole or off the side of a part rather than having the ability to travel over holes and off the edge of a part for inspection. Using conventional part-riding probes, a structure typically is scanned in a manner to go around holes and to not inspect near edges, leaving the edges of the structure to be inspected by a second inspection method, such as by a technician using a manual pulse echo scanning device. Sled appendages, or sleds, of a probe according to the embodiments described here are linear extensions rotatably attached to the bottom of the probe and upon which the probe rides over a surface of the structure. An axial braking system according to the embodiments described here operates to temporarily fix the current positions of the sled appendages to maintain those positions while the probe travels over a hole or off an edge of the structure. An axial braking system may operate in one or more axes. For example, the braking system may lock simply in an x-axis, in both x- and y-axes, or in x-, y-, and z-axes. The axial braking system fixes the position of the sled appendages by locking the axes of motion of the sled appendages before traveling over a hole or off an edge of the structure.

Although in some instances the length of sled appendages may be sufficient to pass over a small hole without needing to use the axial braking system of the probe, the combination of sled appendages and axial braking system are generally provided and used for instances when the probe would otherwise fall through a large hole or off an edge of a structure like a conventional part-riding probe were it not for the operation of the axial braking system to maintain the position of the sled appendages while the probe moves over a hole or off an edge of the structure. Further, by using a probe configured as described herein, a motion control system does not need to maintain or know the precise shape or contour of the structure, but merely the location of holes and edges of the structure so the axial braking system can fix the position of the sled appendages before the probe is passed over a hole or off an edge of the part. Further, although the inspection apparatus described and depicted herein includes two sled appendages located on opposing sides of the inspection apparatus, and an inspection apparatus typically includes two sled appendages, an embodiment of an inspection apparatus might include only a single sled appendage such as a sled appendage with a broad surface width for providing side-to-side balance to the inspection apparatus. Alternative embodiments of an inspection apparatus may include a plurality of sled appendages extending below the inspection apparatus and/or to the sides of the inspection apparatus.

A probe may also include a bubbler shoe. A bubbler shoe according to the embodiments described herein provides a couplant around each transducer for individually coupling each transducer of the probe that remain over the structure for inspection even when other transducers may be over holes or off an edge of the structure. By comparison, conventional coupling shoes typically provide a cavity that surrounds all of the transducers to act as a single couplant for all of the transducers. Thus, if a conventional probe travels over a large hole or off an edge of the part, the water cavity will empty and the ultrasonic signals of all of the transducers may be lost or will be degraded due to the lack of coupling between the structure and the transducers. However, when using a bubbler shoe of an embodiment of the present invention, only the transducers that are over the hole or off the edge of the structure may lose coupling for ultrasonic signals while the transducers remaining over the structure retain the coupling provided by the bubbler shoe.

Figure 2:
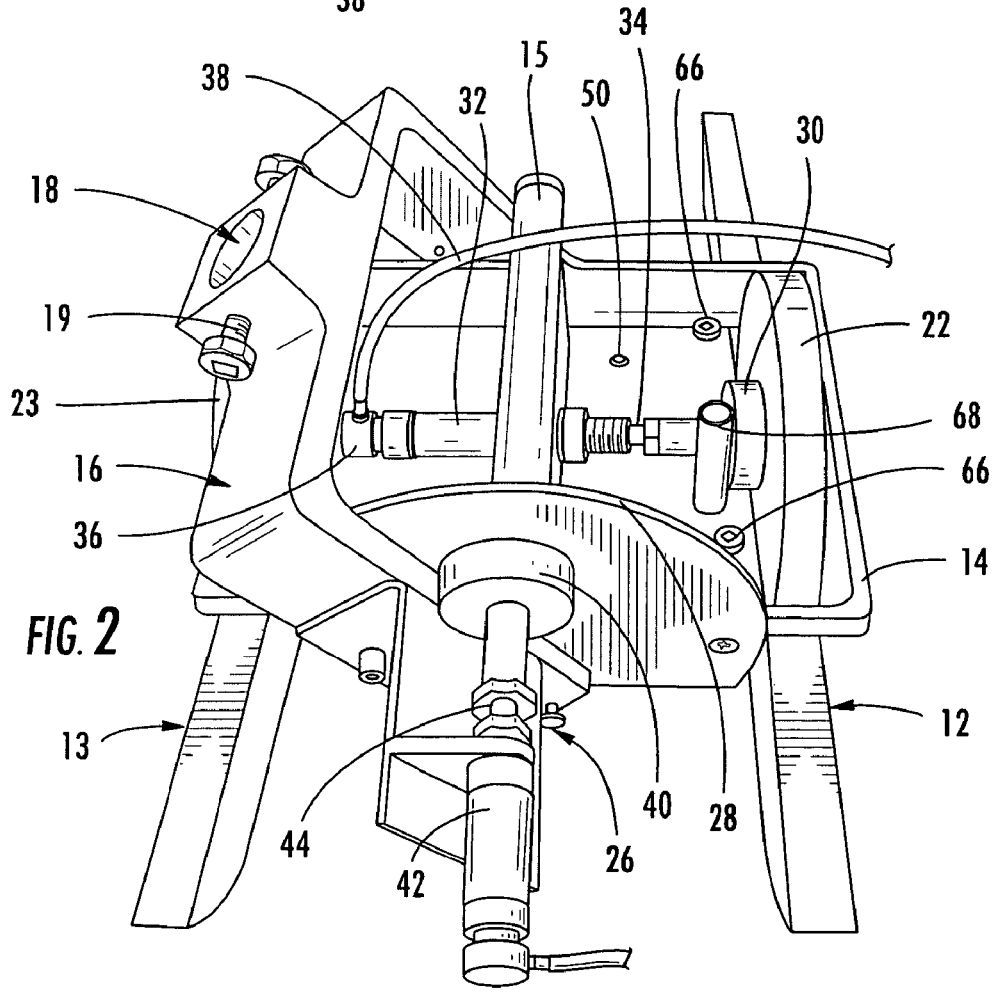
FIG. 2 is another view of the schematic diagram of the inspection apparatus of FIG. 1.

FIGS. 1 and 2 are schematic diagrams of an embodiment of an inspection apparatus, also generally referred to as a probe or inspection probe. The inspection apparatus 10 includes two sled appendages 12, 13 located on opposite sides of the inspection apparatus 10. The sled appendages 12, 13 are rotatably attached to a frame member 14 of the inspection apparatus 10 about a first axis 24 defining a first direction of motion for the sled appendages 12, 13, also referred to as an x-axis, front-to-back tilt axis, or pitch axis. The frame of the inspection apparatus 10 also includes a second frame member 16 which is rotatably connected to the first frame member 14 about a second axis 26 defining a second direction of motion for the sled appendages 12, 13, also referred to as a y-axis, side-to-side slant axis, or roll axis. By having two rotational axes, the sled appendages 12, 13 are capable of rotating in at least two directions of motion with respect to a motion control system connected to the inspection apparatus 10, such as by way of an attachment at the opening 18 and securing screws 19, to compensate for surface variations of the structure, such as shape and contour characteristics of the surface. Further, because as described below, a transducer holder or bubbler shoe for an embodiment of an inspection apparatus is connected to sled appendages, rather than the frame, the transducers maintain the same position and orientation as achieved by the sled appendages, thereby providing the transducers a consistent orientation with respect to the surface of the structure over which the inspection apparatus rides on the sled appendages. Maintaining a consistent orientation, distance and angle, of the transducers with respect to the surface of the structure ensures consistent quality of inspection by the transducers.

At least one of the sled appendages 12, 13 includes an upper portion 22, 23 that functions as a stationary brake plate against which a brake disc 30 of the axial braking system can be applied to fix the position of the sled appendage about the first axis of motion 24. An axial braking system of an embodiment may also include a pneumatic brake cylinder 32 with an extendable piston arm 34 to which a brake disc 30 is attached at the distal end of the extendable piston arm 34 protruding from the brake cylinder 32. A brake cylinder 32 may be activated by any conventional method, such as by compressing a fluid, typically air, through a supply line 38 into a valve 36 attached to the brake cylinder 32. When the brake mechanism is activated, the compression of fluid causes a piston inside the brake cylinder 32 and attached to the distal end of the extendable piston arm 34 inside the brake cylinder 32 to force the extendable piston arm 34 out of the brake cylinder 32 to force the brake disc 30 to press against the stationary brake plate 22, 23 of one or more sled appendages 12, 13.

To fix the position of the sled appendages in the second axis of motion 26, a second brake plate 28 may be affixed to the first frame member 14 to permit a second brake mechanism 40, 42, 44, 46, 48, to engage the second stationary brake plate 28 in the same manner that the first brake mechanism 30, 32, 34, 36, 38 engages the first stationary brake plate 22, 23 to fix the position of the sled appendages 12, 13 about the first axis of motion 24. The first frame member 14 may include a vertical support member 15 connected to the second stationary brake plate 28 to provide stability between the first frame member 14 and the second stationary brake plate 28, such as when a brake disc 40 is pressed against the second stationary brake plate 28 to fix the position of the sled appendages in the second axis of motion 26. An axial braking system of an alternative embodiment may also include a brake mechanism in a third direction of motion, such as a vertical z-axis with respect to the surface of the structure, and may be incorporated into an attachment to a motion control system.

To improve braking capabilities of a braking system, brake discs and/or stationary brake plates may be coated with or include an attached layer of material, such as being coated with rubber, to cause increased friction between a brake disc and stationary brake plate for fixing the positions of sled appendages and preventing slippage of the positions of the sled appendages.

The inspection apparatus 10 includes at least one pulse echo ultrasonic transducer 50. If not using a couplant between the transducers 50 of the inspection apparatus 10 and the structure, a transducer holder may be attached to the sled appendages 12, 13 to support the transducers 50, such as supported in an array where a plurality of transducers are used to increase the inspection coverage area. As mentioned above, by attaching the transducer holder, or bubbler shoe as described below, to the sled appendages 12, 13 the transducer holder and transducers 50 supported thereby also maintain constant orientation with the surface of the structure over which the inspection apparatus 10 rides because the inspection apparatus 10 rides over the surface of the structure on the sled appendages 12, 13. Because inspection of a structure typically requires ensuring that the transducers maintain constant orientation, distance and angle, with respect to the surface of the structure, attaching a transducer holder, or bubbler shoe, to sled appendages ensures that the transducer holder, or bubbler shoe, and transducers supported thereby also maintain constant orientation with respect to the surface of the structure for consistent quality of inspection by the transducers.

If a couplant is to be used to couple the ultrasonic signals from the transducers 50 into the structure and reflected from the structure back to the transducers 50, a bubbler shoe 60 may be incorporated into the inspection apparatus 10. The bubbler shoe 60 individually couples each transducer 50 rather than using a single cavity to couple all of the transducers 50. A bubbler shoe may include a top (or first) layer 62 that includes holes 64 to permit access to the transducers 50, such as by the transducer protruding through the holes 64 in the top layer 62 or by permitting a wired connection through the holes 64 in the top layer 62 for communication with the transducers 50. The top layer 62 may also include one or more fluid inlets 68, 69 through which a couplant may be injected into the bubbler shoe 60. The bubbler shoe 60 may also include a bottom (or second) layer that, together with the top layer 62, define a cavity through which a couplant from the fluid inlet 68, 69 can flow to individually couple each transducer 50. By way of example, such cavities may be a single open cavity providing a fluid path to each transducer or may be a cavity structured with a manifold configuration whereby the couplant passes into separate subcavities that lead to the individual transducers. The bottom layer includes holes through which the couplant passes to couple the transmission of ultrasonic signals from the transducers 50. The transducers 50 may pass through the holes in the bottom layer, may terminate inside the cavity, or may terminate within the bottom layer.

Figure 3A:
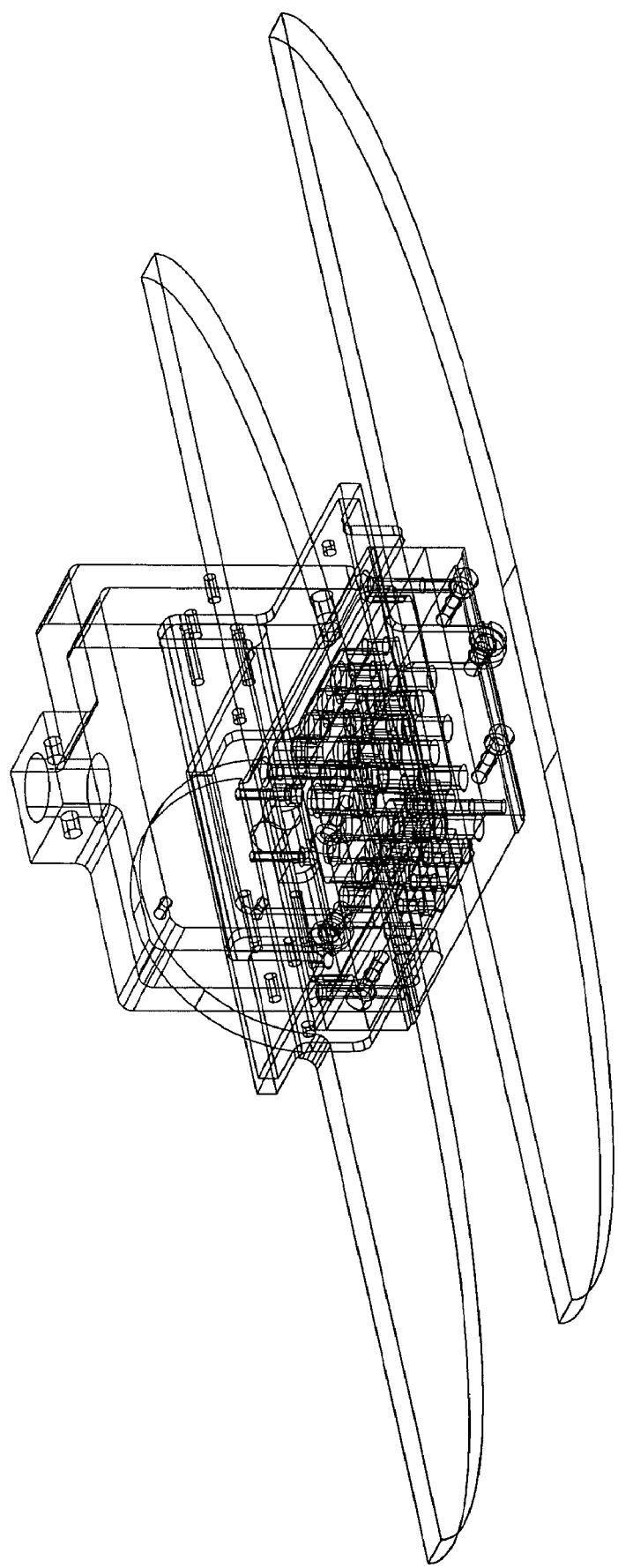
FIG. 3A is a schematic diagram of another embodiment of an inspection apparatus.
Figure 3B:
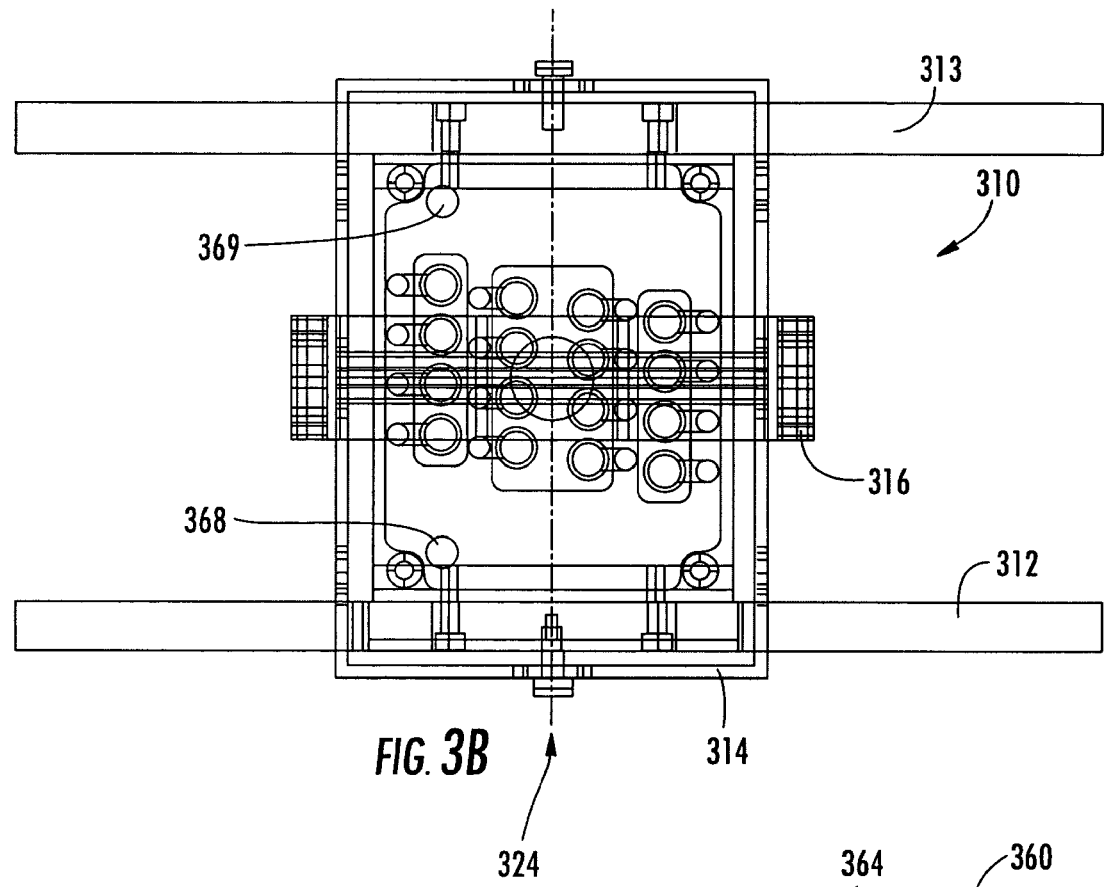
FIG. 3B is a top plan view of the inspection apparatus of FIG. 3A.
Figure 3C:
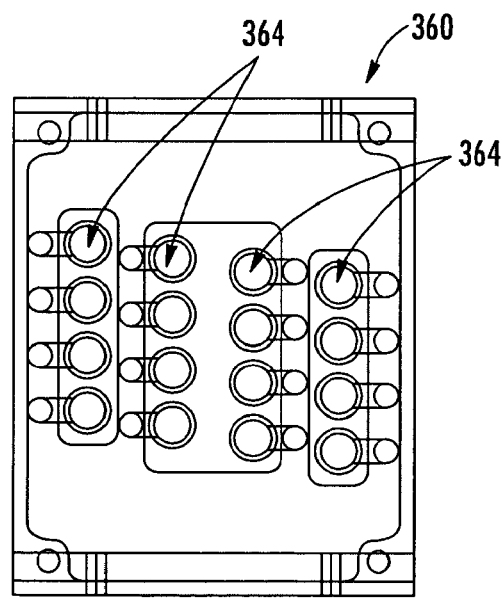
FIG. 3C is a top plan view of the bubbler shoe of the inspection apparatus of FIG. 3A.

FIG. 3A is a schematic diagram of another embodiment of an inspection apparatus. FIG. 3B is a top plan view of the inspection apparatus of FIG. 3A. FIG. 3C is a top plan view of the bubbler shoe of the inspection apparatus of FIG. 3A. The inspection apparatus 310 of FIGS. 3A, 3B, and 3C differs from an inspection apparatus 10 of FIGS. 1 and 2 in that the inspection apparatus 310 of FIGS. 3A, 3B, and 3C provides only one axis of motion 324 for the sled appendages 312,313, while the inspection apparatus 10 of FIGS. 1 and 2 provides two axes of motion 24, 26 for the sled appendages 12, 13. Although a bubbler shoe 60 with a transducer array is present in the inspection apparatus 10 of FIGS. 1 and 2, FIGS. 3A, 3B, and 3C clearly show an example configuration for an array of transducers in the bubbler shoe 360 of the inspection apparatus 310. While the internal construction of the bubbler shoe 360 is visible to some extent in FIG. 3A, FIG. 4 clearly shows an example internal construction of another bubbler shoe 460.

Figure 4:
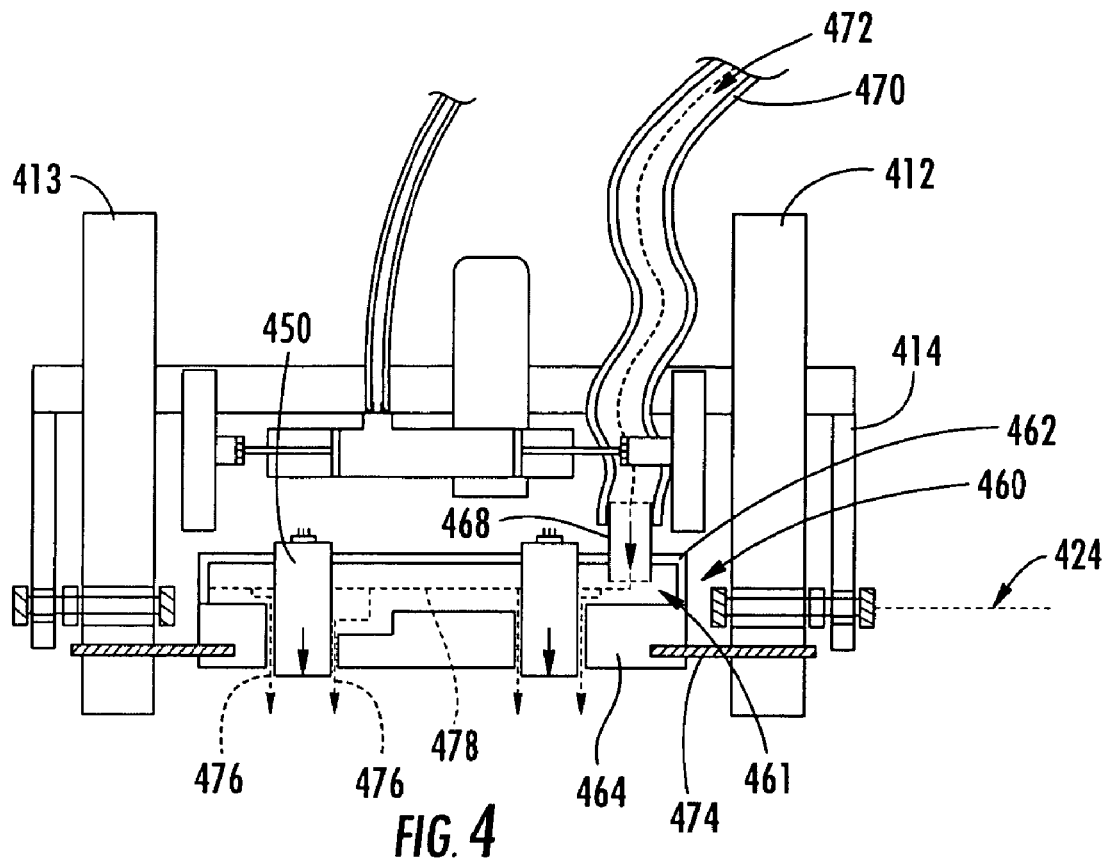
FIG. 4 is a cross-section of a schematic diagram of yet another embodiment of an inspection apparatus.

FIG. 4 is a cross-section of a schematic diagram of yet another embodiment of an inspection apparatus. The cross-section represents an approximate mid-point through a first axis of rotation 424 corresponding to the front-back tilt of the sled appendages 412, 413. The cross-sectional view shows the internal structure of one embodiment of a bubbler shoe 460 for individually coupling each transducer 450. The bubbler shoe 460 includes a top layer 462 and a bottom layer 464 configured together to form a cavity 461 into which a couplant is injected for being dispersing about the cavity 461 and, after filling the cavity 461, being evenly dispersed around each of the transducers 450 to couple the ultrasonic signals from the transducers 450 to the structure. A fluid couplant path 472 passes through a supply line 470 into and through a fluid inlet 486 into the bubbler shoe 460. The couplant path continues to disperse throughout the cavity 461 as indicated by the fluid couplant path 478. The ejection of the couplant from the cavity 461 of the bubbler shoe 460 around each of the transducers 450 is indicated by fluid couplant paths 476. Typically water may be used for a couplant, but other fluids may be used.

The cross-section of the inspection apparatus of FIG. 4 also shows how the bubbler shoe 460 may be connected to the sled appendages 412, 413 to maintain constant orientation with respect to the structure by the bubbler shoe 460 and transducers 450 supported thereby. The connection 474 between the sled appendages 412, 413 and the bottom layer 464 of the bubbler shoe 460 provides a non-rotational connection between the bubbler shoe 460 and the sled appendages 412, 413. By comparison to the first axis of motion 424, the connection 474 is not a rotational axis that provides a direction of motion but is fixed to provide the same orientation with respect to the structure that the sled appendages 412, 413 have to the bubbler shoe 460 and transducers 450 supported thereby.

Figure 5:
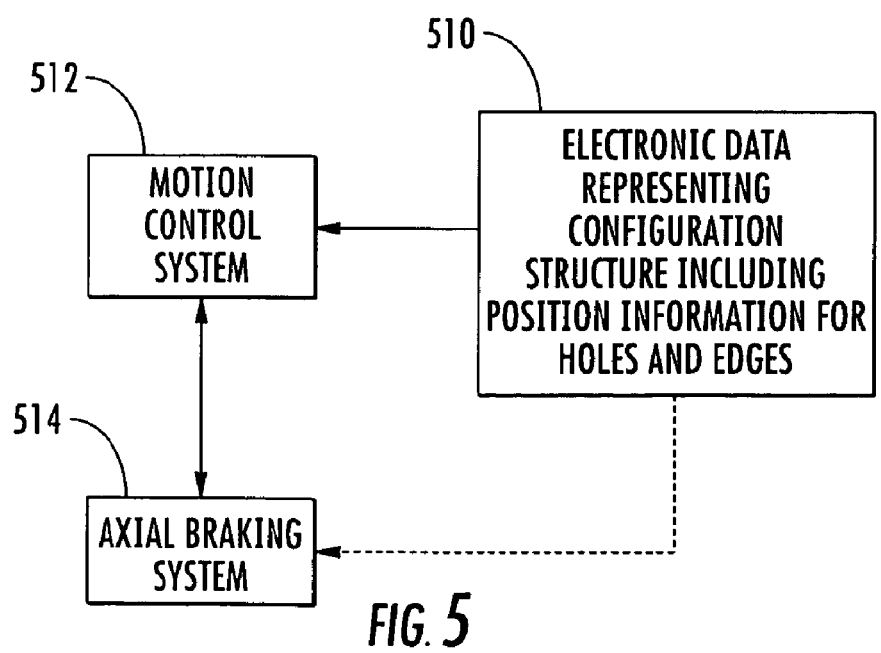
FIG. 5 is a block diagram of an embodiment of an inspection system.

FIG. 5 is a block diagram of an embodiment of an inspection system. The block diagram shows communication between a motion control system 512 and an axial braking system 514. In addition, electronic data 510 representing the configuration of the structure under inspection, including position information for holes in edges of the structure, is provided to the motion control system 512. An alternative embodiment for an inspection system may include an axial braking system that incorporates hardware and software to interpret the position of the inspection apparatus with respect to holes and edges of the structure, referred to as a smart axial braking system. For example, a smart axial braking system may include some form of a position encoder or positioning system that operates to identify the location of the inspection apparatus with respect to the structure and electronic data representing the configuration of the structure, such as the electronic data 510 provided to the motion control system in the embodiment shown in FIG. 5.

The axial braking system 514 may be activated based on data provided by the motion control system 512. For example, the motion control system 512 may incorporate software that interprets the position of the inspection apparatus with respect to holes in edges of the structure and indicate to the axial braking system 514 when to activate the braking mechanisms on an inspection apparatus to fix the positions of sled appendages on the inspection apparatus and when to deactivate the braking mechanisms. For example, when the motion control system 512 identifies that the inspection apparatus is about to travel over a hole, the motion control system 512 can communicate to the axial braking system 514 to fix the current position of the sled appendages for while the inspection apparatus travels over the hole. When the motion control system 512 determines that the inspection apparatus has passed over the hole, the motion control system 512 may communicate to the axial braking system 514 to release the sled appendages so they may continue to ride along and follow the contoured surface of the structure. For example, a solenoid actuated pneumatic switch of the axial braking system 514 may activate to apply pressure to a pneumatic brake cylinder to extend brake discs against stationary brake plates on the sled appendages. The activation of the solenoid actuated pneumatic switch may be controlled by output signals provided by the motion control system 512 to indicate to the axial braking system 514 to fix the positions of the sled appendages.

Alternatively, the motion control system 512 may provide location data of the inspection apparatus with respect to a structure being inspected to the axial braking system 514, and the axial braking system 514 may use the location data, in addition to electronic data 510 representing the configuration of the structure either provided through the motion control system 512 or directly to the axial braking system 514, to determine when the axial braking system 514 should activate braking mechanics on the inspection apparatus to fit the positions of sled appendages, such as before traveling over a hole or off an edge of the structure.

Figure 6:
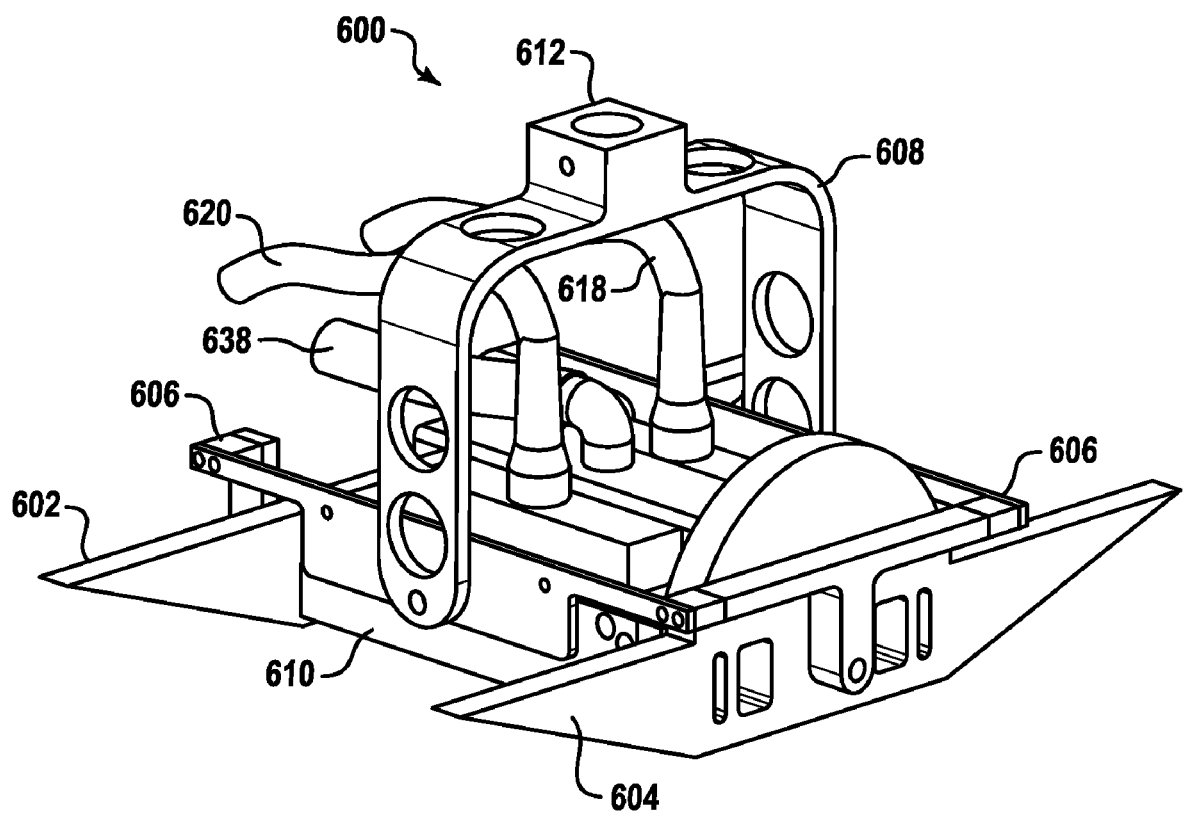
FIG. 6 is a perspective view of an alternate embodiment of an inspection apparatus.
Figure 7:
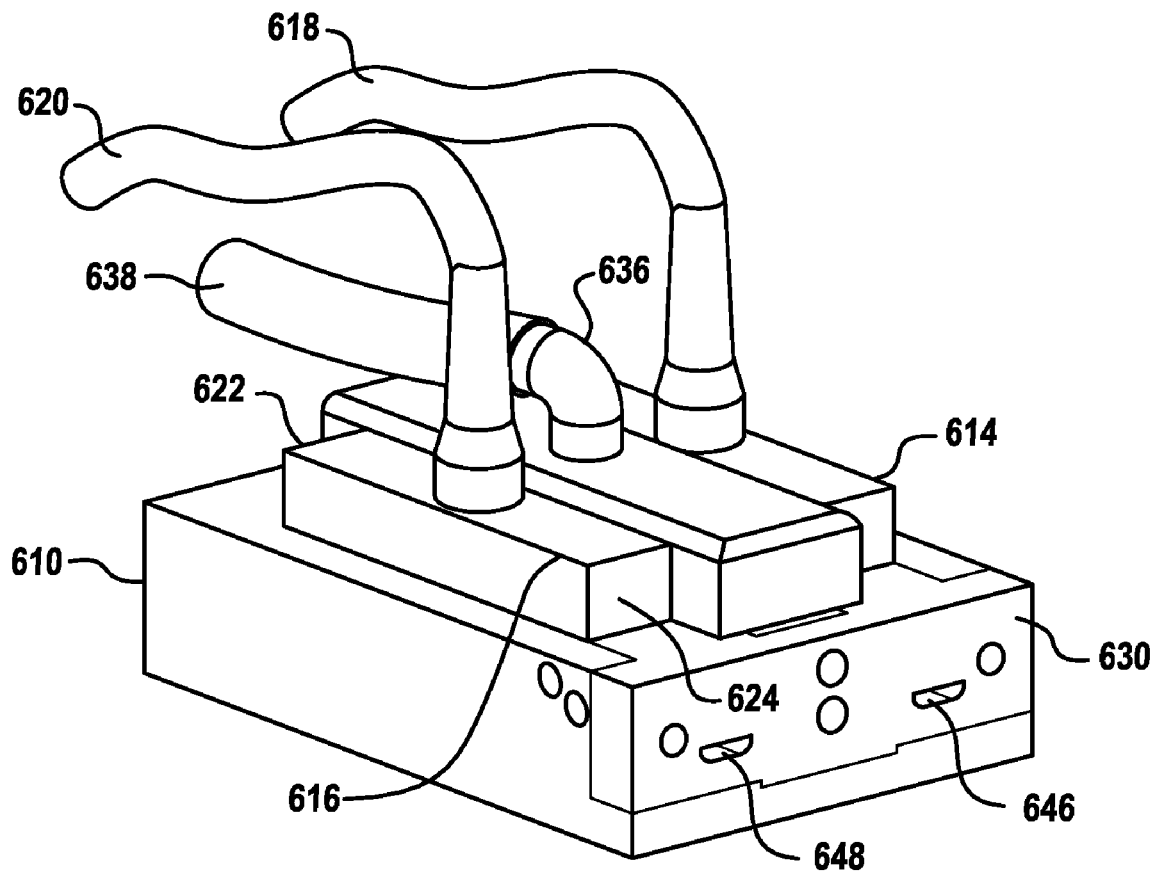
FIG. 7 is a perspective view of a support body and two ultrasonic transducer arrays suitable for use with the inspection apparatus shown in FIG. 6.
Figure 8:
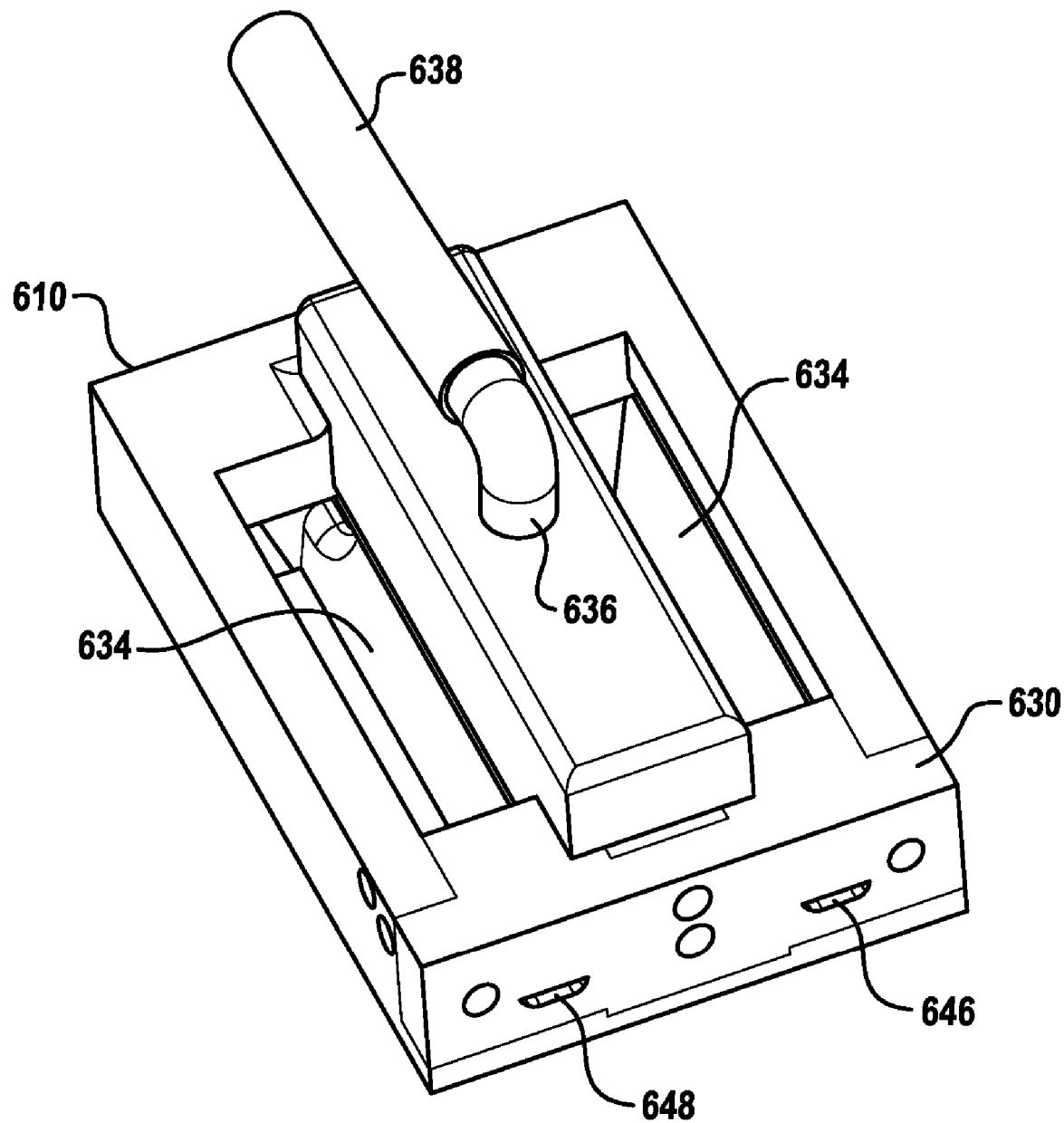
FIG. 8 is a perspective top view of the support body shown in FIG. 7, with the two ultrasonic transducer arrays removed.
Figure 9:
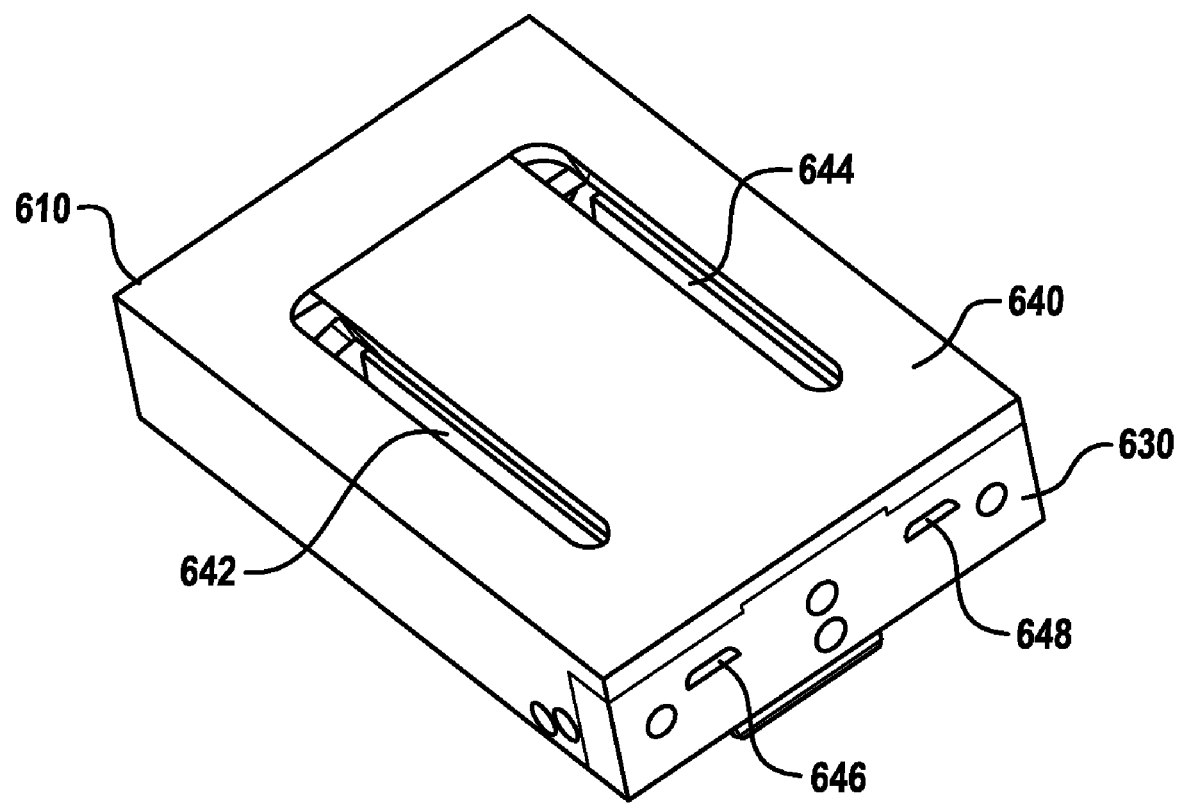
FIG. 9 is a perspective bottom view of the support body shown in FIG. 7.
Figure 10:
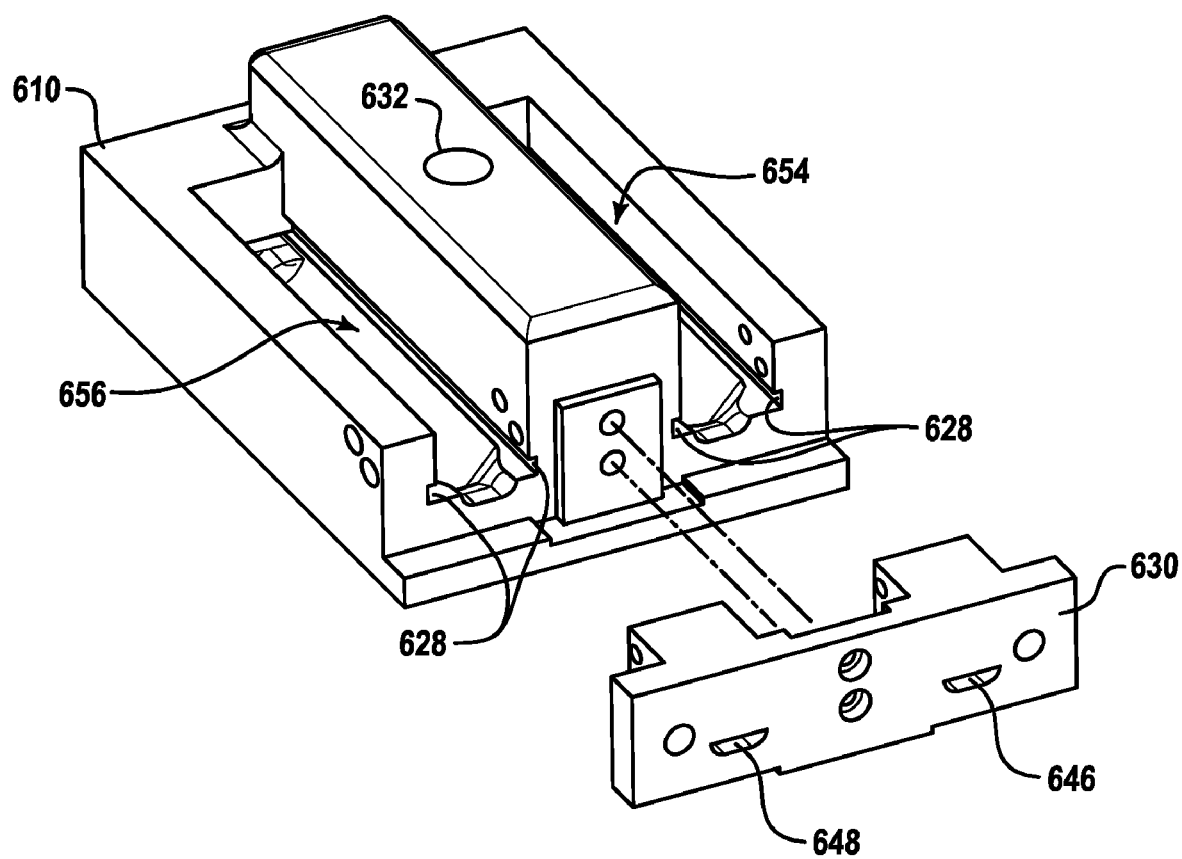
FIG. 10 is a perspective top view of the support body shown in FIG. 8, with the end cap removed.
Figure 11:
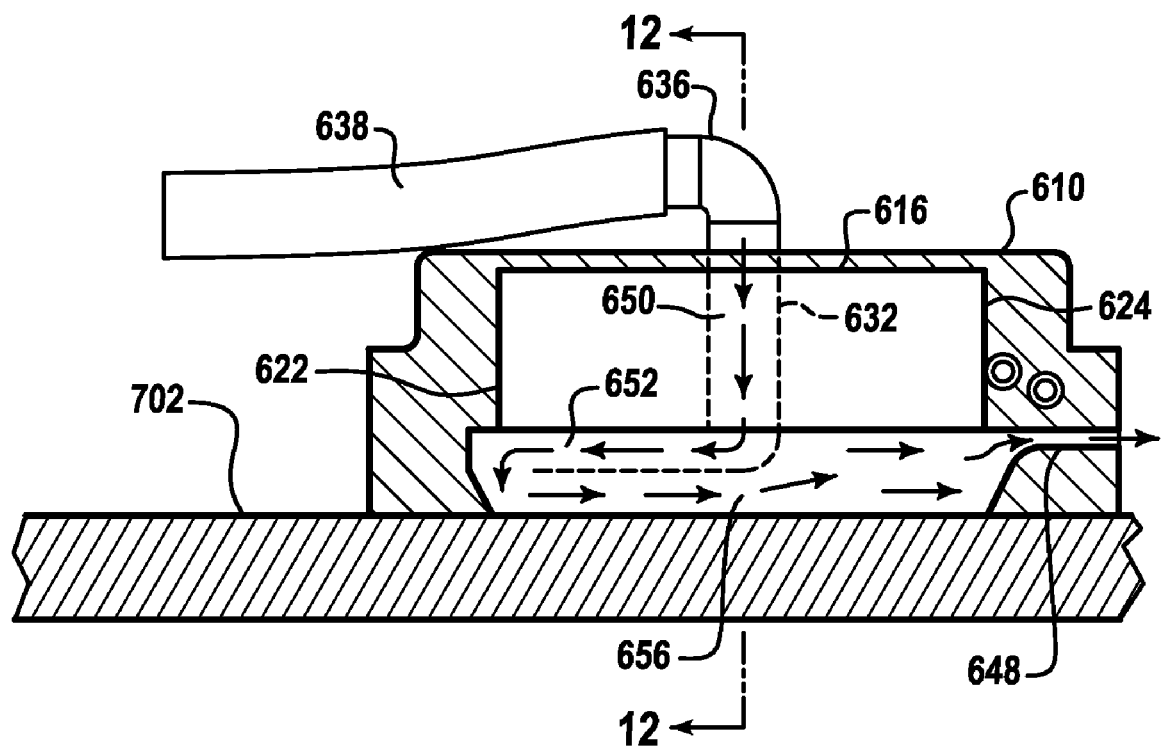
FIG. 11 is a side and partially phantom view of the support body shown in FIG. 7.
Figure 12:
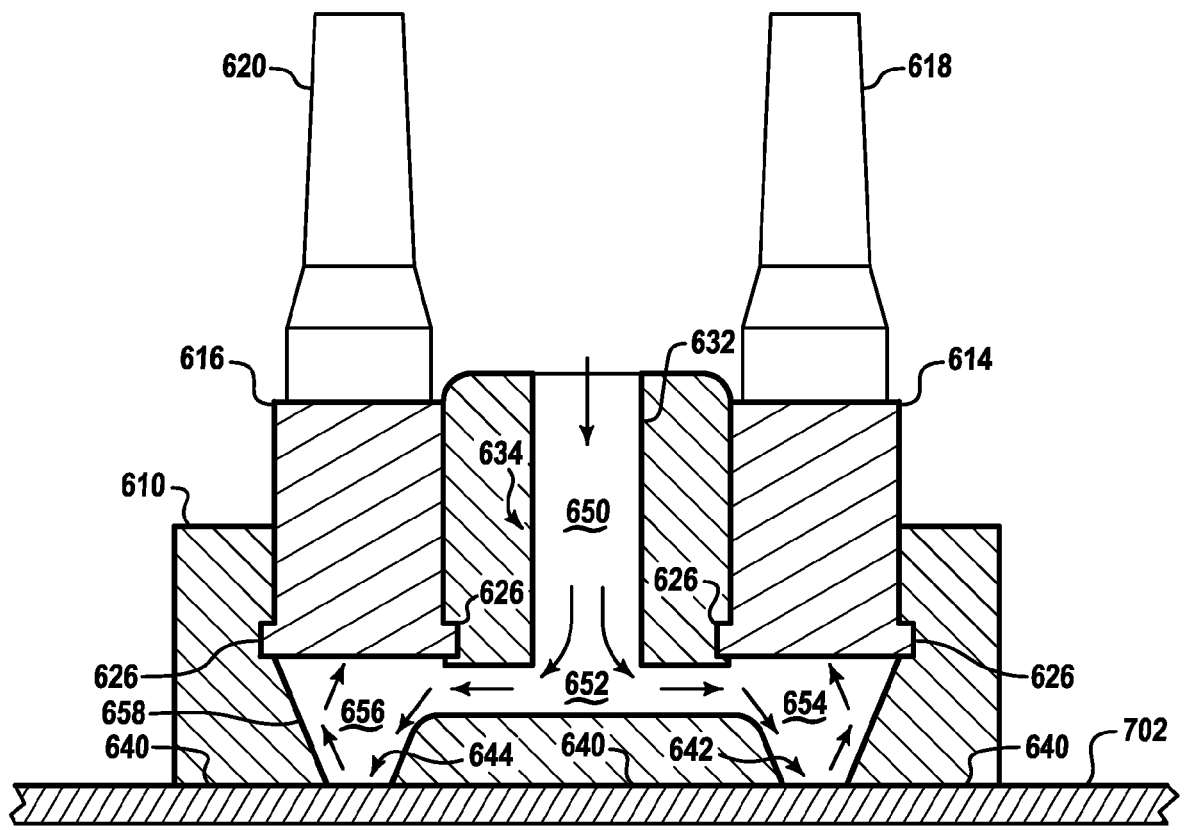
FIG. 12 is a schematic cross sectional view of the support body shown in FIG. 11, viewed from line 12-12.
Figure 13:
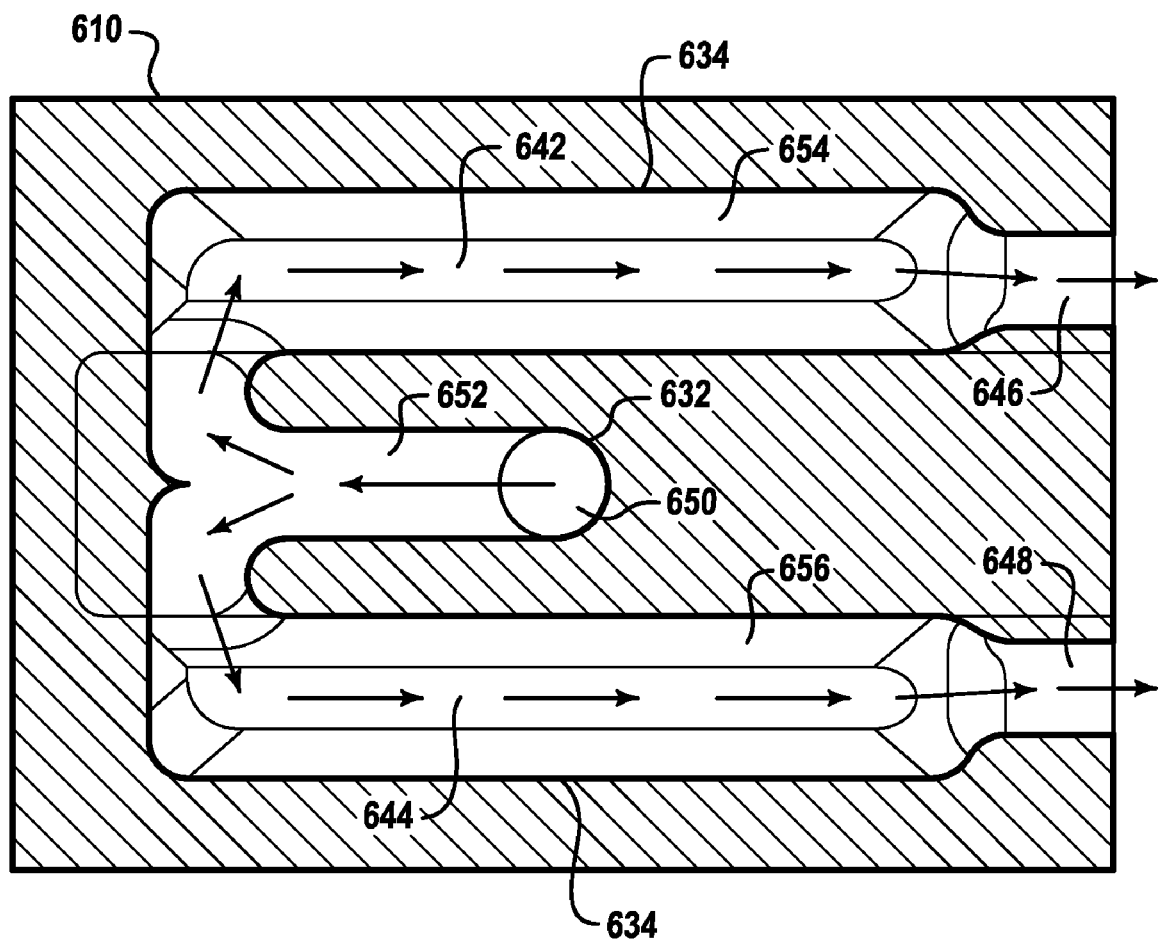
FIG. 13 is a schematic phantom top view of the support body shown in FIG. 7, FIG. 11, and FIG. 12, depicting the projected outline of a fluid conduit.

FIG. 6 is a perspective view of an alternate embodiment of an inspection apparatus 600 that can be utilized in an ultrasonic inspection system. Inspection apparatus 600 is similar in some respects to the inspection apparatus described above with reference to FIGS. 1-4, and common elements, features, functions, and operations will not be redundantly described here in the context of inspection apparatus 600. Inspection apparatus 600 generally includes, without limitation: sled appendages 602/604; a first frame member 606; a second frame member 608; and a support body 610. FIG. 7 is a perspective view of support body 610 and two ultrasonic transducer arrays suitable for use with inspection apparatus 600, FIG. 8 is a perspective top view of support body 610 with the two ultrasonic transducer arrays removed, FIG. 9 is a perspective bottom view of support body 610, FIG. 10 is a perspective top view of support body 610 with its end cap removed, FIG. 11 is a side and partially phantom view of support body 610, FIG. 12 is a schematic cross sectional view of support body 610 viewed from line 12-12 in FIG. 11, FIG. 13 is a schematic phantom top view of support body 610 that depicts the projected outline of a fluid conduit within support body 610, and FIG. 14 is a schematic representation of an embodiment of an ultrasonic inspection system 700 that employs inspection apparatus 600.

Figure 14:
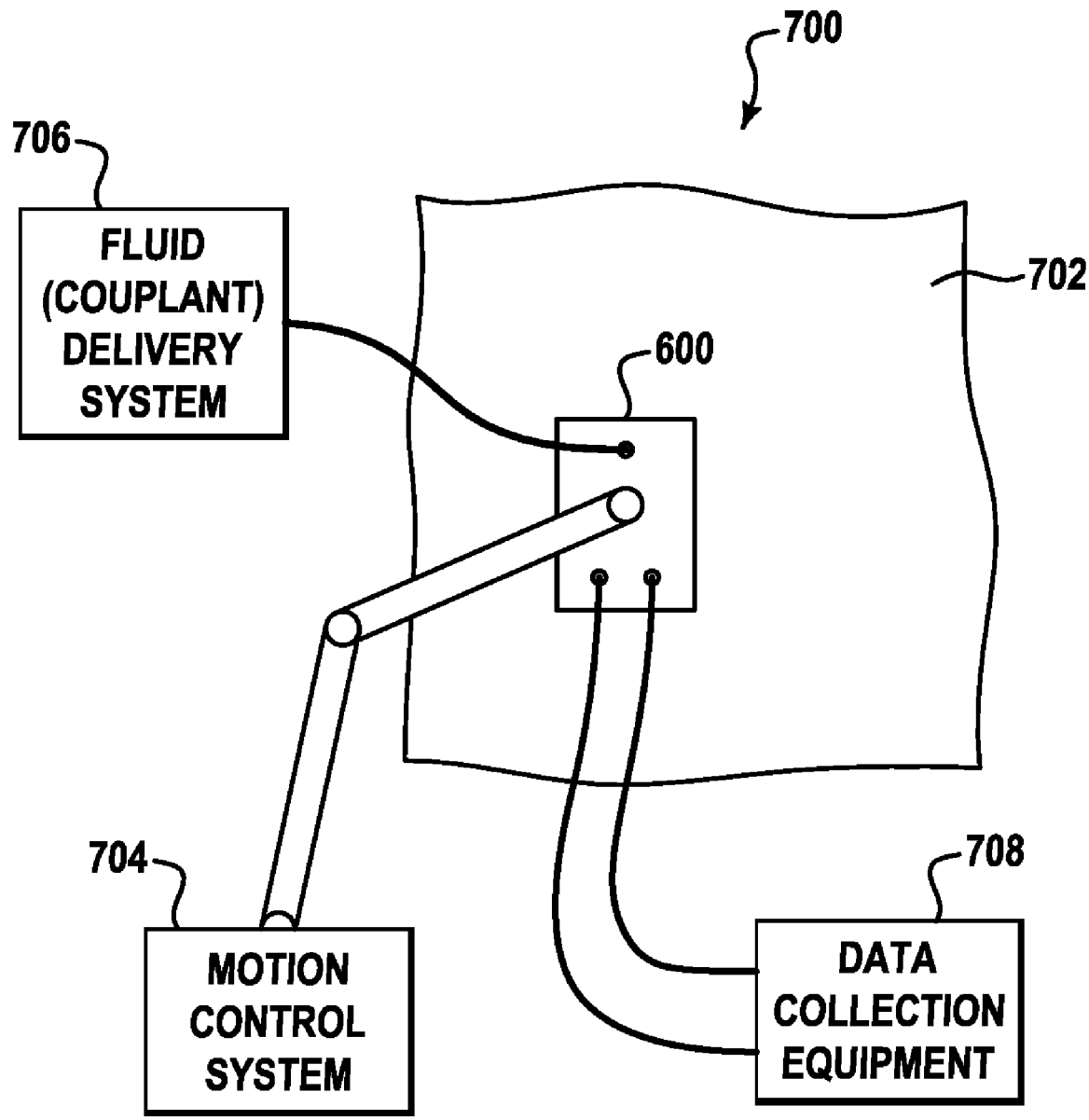
FIG. 14 is a schematic representation of an embodiment of an ultrasonic inspection system.

Referring to FIG. 14, ultrasonic inspection system 700 can be utilized to ultrasonically inspect the surface of a structure 702. This embodiment of system 700 includes, without limitation: inspection apparatus 600; a motion control device, system, or subsystem 704; a fluid delivery device, system, or subsystem 706; and data collection equipment 708. Inspection apparatus 600 is coupled to motion control subsystem 704 such that motion control subsystem 704 can move inspection apparatus 600 over the surface of structure 702 during testing. Fluid delivery subsystem 706, which is coupled to a fluid inlet of inspection apparatus 600, is suitably configured to deliver a couplant (e.g., water or another fluid) to inspection apparatus 600 as described in more detail herein. In operation, fluid delivery subsystem 706 provides the couplant at a desired pressure and flow rate. For this embodiment, fluid delivery subsystem 706 provides the couplant at a rate of about one to three gallons per minute. Data collection equipment 708, which is coupled to ultrasonic transducer arrays held by inspection apparatus 600, is suitably configured to generate and receive test signals corresponding to the ultrasonic transducer arrays.

Referring again to FIG. 6, second frame member 608 includes an attachment feature 612 for motion control subsystem 704, which moves inspection apparatus 600 over structure 702 for purposes of inspection. Attachment feature 612 enables inspection apparatus 600 to be coupled to motion control subsystem 704 as needed for a test procedure. Support body 610 is coupled to sled appendages 602/604, first frame member 606, and second frame member 608, which cooperate to form a gimbal mechanism for support body 610. For this embodiment, the contact surfaces of sled appendages 602/604 are substantially coplanar with the contact surface of support body 610. Alternatively, the contact surfaces of sled appendages 602/604 can be slightly offset from the contact surface of support body 610 such that a thin gap is formed between the structure under test and the contact surface of support body 610 (in operation, fluid delivery subsystem 706 would fill this thin gap with the couplant).

Notably, inspection apparatus 600 is configured to receive and hold a plurality of ultrasonic transducer arrays, which are configured to simultaneously inspect structure 702 using a plurality of frequencies as inspection apparatus 600 is moved over and along structure 702. This particular embodiment of inspection apparatus 600 includes two ultrasonic transducer arrays coupled to support body 610: a high frequency array 614 and a low frequency array 616. High frequency array 614 includes a plurality of ultrasonic transducers, and high frequency array 614 is configured to inspect structure 702 at a relatively high ultrasonic frequency as support body 610 is moved over structure 702. Low frequency array 616 includes a plurality of ultrasonic transducers, and low frequency array 616 is configured to inspect structure 702 at a relatively low ultrasonic frequency as support body 610 is moved over structure 702. For this embodiment, the high frequency is 3.5 MHz (which is suitable for the ultrasonic inspection of structure 702 for relatively low porosity conditions) and the low frequency is 1.5 MHz (which is suitable for the ultrasonic inspection of structure 702 for relatively high porosity conditions). In practice, the number of ultrasonic transducer arrays and the respective operating frequencies can be selected according to the particular testing requirements, the configuration or composition of the structure under test, and/or other considerations.

High frequency array 614 is coupled to data collection equipment 708 using a cable 618 that includes wires for the ultrasonic transducers in high frequency array 614. Similarly, low frequency array 616 is coupled to data collection equipment 708 using a cable 620 that includes wires for the ultrasonic transducers in low frequency array 616. During inspection, data collection equipment 708 generates and simultaneously transmits high frequency and low frequency ultrasonic test signals to the respective ultrasonic transducer arrays 614/616. In response to the test signals, the arrays 614/616 generate and transmit corresponding high frequency and low frequency ultrasonic detection signals, which are received by data collection equipment 708. As described in more detail below, a couplant such as water is used to couple high frequency ultrasonic signals between high frequency array 614 and structure 702, and to couple low frequency ultrasonic signals between low frequency array 616 and structure 702. Notably, data collection equipment 708 independently receives the set of detection signals from high frequency array 614 via cable 618, and independently receives the set of detection signals from low frequency array 616 via cable 620. Data collection equipment 708 (or other equipment that receives data from data collection equipment 708) can then process the detection signals in an appropriate manner to determine the characteristics of structure 702.

Arrays 614/616 may be configured to transmit and receive their respective ultrasonic signals simultaneously and at the same time, concurrently during a time period, and/or in an interleaved manner during a time period. In practice, the use of two or more ultrasonic transducer arrays as described herein facilitates quick ultrasonic inspection of structure 702 in only one pass. In contrast, conventional inspection systems require multiple passes to inspect a structure using multiple frequencies (i.e., N passes for N different frequencies).

Referring also to FIG. 11, ultrasonic transducer array 616 has an elongated shape with a first end 622 and a second end 624 (ultrasonic transducer array 614 is similarly configured and will not be separately described here). Array 616 carries a plurality of ultrasonic transducers, which are arranged between first end 622 and second end 624. In this embodiment, array 616 includes 64 transducers arranged in a linear pattern. Of course, different transducer configurations, numbers, and topologies may be employed in an embodiment of inspection apparatus 600. Notably, inspection apparatus 600 is preferably moved in a direction that is perpendicular to the major longitudinal axis of array 614 during testing.

Referring to FIG. 10 and FIG. 12, support body 610 is suitably configured to receive and hold ultrasonic transducer arrays 614/616, which are preferably manufactured as distinct standalone components. Arrays 614/616 are held such that their faces are parallel with the contact surface of support body 610 (which in operation approximately corresponds to the surface of structure 702 being tested. In this embodiment, each array 614/616 has two longitudinal feet or protrusions 626 (FIG. 12) that are located at or near the base of the array. These protrusions 626 correspond to respective registration elements 628 (FIG. 10) formed within support body 610. Registration elements 628 may be realized as longitudinal slots, as shown in FIG. 10, that serve as keyways for protrusions 626. Thus, arrays 614/616 are slid into place using registration elements 628, and an end cap 630 is attached to support body 610 to maintain arrays 614/616 in position. In practice, end cap 630 is secured to support body 610 using screws, clips, bolts, or any suitable fastening mechanism. As shown in FIG. 12, registration elements 628 and protrusions 626 cooperate to hold arrays 614/616 away from the surface of structure 702 during inspection.

Support body 610 is formed from a one-piece material, such as a piece of nylon stock. As described in more detail herein, support body 610 includes a number of internal features formed therein. In practice, such internal features are formed using a rapid prototyping process. Rapid prototyping processes, including laser cutting techniques, are well known to those skilled in the art and, therefore, such processes will not be described in detail here. End cap 630 may also be formed from nylon, using a rapid prototyping process.

As mentioned above, inspection apparatus 600 receives a fluid couplant such as water from fluid delivery subsystem 706 (FIG. 14). In this regard, support body 610 includes a fluid inlet 632 and a fluid conduit 634 in communication with fluid inlet 632. In the illustrated embodiment, fluid inlet 632 and fluid conduit 634 are both integrally formed within support body 610. Moreover, inspection apparatus 600 includes a fitting 636 for a hose 638 (or any suitable conduit for the couplant), where fitting 636 is coupled to fluid inlet 632 and hose 638 leads to fluid delivery subsystem 706. Fluid inlet 632 and fluid conduit 634 are configured to transport the couplant to ultrasonic transducer arrays 614/616, as regulated by fluid delivery subsystem 706. In particular, fluid conduit 634 is shaped and sized to promote the flow of the couplant from fluid inlet 632, to a location proximate the ends of arrays 614/616, across arrays 614/616, and to a location proximate the opposite ends of arrays 614/616.

Referring to FIGS. 9, 12, and 13, support body 610 includes a base 640 having formed therein an opening 642 corresponding to array 614 and another opening 644 corresponding to array 616. As depicted in FIG. 12, support body 610 is suitably configured to hold the transducers in arrays 614/616 away from the respective openings 642/644. These openings 642/644 accommodate the ultrasonic energy generated by arrays 614/616. Consequently, openings 642/644 are preferably sized and shaped as longitudinal slots that generally follow the arrangement of transducers found in arrays 614/616. Referring to FIG. 12, the lowermost features (e.g., the bottom surfaces) of arrays 614/616 define at least a portion of fluid conduit 634, and the couplant flows within fluid conduit 634 such that it fills the space between arrays 614/616 and openings 642/644. In this manner, fluid conduit 634 is designed to disperse the couplant between arrays 614/616 and the surface under test. In operation, when inspection apparatus 600 is held against structure 702, the surface of structure 702 helps to retain the couplant in this space.

Referring to FIGS. 9-11 and 13, inspection apparatus 600 also includes at least one relief port for fluid conduit 634, where the at least one relief port is configured to accommodate the ejection of couplant (along with gas bubbles that might be contained in the couplant) from fluid conduit 634. The illustrated embodiment includes one relief port 646 that generally corresponds to ultrasonic transducer array 614, and another relief port 648 that generally corresponds to ultrasonic transducer array 616. During an inspection operation, fluid delivery subsystem 706 maintains the couplant under sufficient pressure such that at least some of the couplant, and gas bubbles contained therein, is ejected out of fluid conduit 634 via relief ports 646/648.

In practice, fluid conduit 634 is defined by: cavities, channels, and features formed within support body 610 itself; the lowermost feature of array 614; and the lowermost feature of array 616. Fluid conduit 634 terminates at relief ports 646/648 and at openings 642/644. However, when inspection apparatus 600 is pressed against structure 702 (as shown in FIG. 12), fluid conduit 634 is also defined by the surface of structure 702 that covers openings 642/644. Referring to FIGS. 10-13, fluid conduit 634 generally includes: an inlet path 650; a feed path 652; a longitudinal flow channel 654 for ultrasonic transducer array 614; and a longitudinal flow channel 656 for ultrasonic transducer array 616. Inlet path 650 is in fluid communication with fluid inlet 632, and feed path 652 is in fluid communication with inlet path 650. As depicted in FIG. 11, inlet path 650 is a straight path from fluid inlet 632 into support body 610, and feed path 652 is generally orthogonal to inlet path 650. As depicted in FIG. 12 and FIG. 13, feed path 652 splits and feeds both longitudinal flow channels 654/656. Longitudinal flow channel 654 runs under array 614 and terminates at relief port 646. Similarly, longitudinal flow channel 656 runs under array 616 and terminates at relief port 648.

The arrows in FIGS. 11-13 represent the general flow path of the couplant through fluid conduit 634. Inlet path 650 carries the couplant from fluid inlet 632 to a location deeper within support body 610. Feed path 652 carries the couplant from the location below fluid inlet 632 to a location near one end of arrays 614/616 (near the left side of support body 610 in FIG. 11 and FIG. 13). As best shown in FIG. 13, feed path 652 splits into longitudinal flow channels 654/656. This allows inspection apparatus 600 to provide individual columns of couplant for the respective arrays 614/616, via openings 642/644. The couplant in longitudinal flow channel 654 flows from the end near feed path 652 to the end near relief port 646, and the couplant in longitudinal flow channel 656 flows from the end near feed path 652 to the end near relief port 648. In this embodiment, each relief port 646/648 is sized and shaped to restrict fluid flow relative to its respective longitudinal flow channel 654/656. In this regard, relief ports 646/648 are thinner (see FIG. 11) and narrower (see FIG. 13) relative to longitudinal flow channels 654/656. This restrictive configuration ensures that the couplant can be maintained at a desirable pressure within support body 610.

As depicted in FIG. 10 and FIG. 12, each longitudinal flow channel 654/656 includes chamfered sidewalls 658 that are located between the two ends of ultrasonic transducer arrays 614/616. As best shown in FIG. 12, the outer sidewalls are angled towards the center of support body 610 as they approach openings 642/644, while the inner sidewalls are angled away from the center of support body 610 as they approach openings 642/644. In other words, longitudinal flow channels 654/656 are wider near arrays 614/616, and are narrower near openings 642/644. In the illustrated embodiment, chamfered sidewalls 658 terminate at openings 642/644. This tapered sidewall configuration is desirable to prevent turbulence and to direct sound (ultrasonic signals) to the desired location. The tapered sidewalls also reduces the required water volume compared to a non-tapered configuration.

During an inspection procedure, inspection apparatus 600 can be held in a horizontal, vertical, or other orientation. When held in a vertical (or any non-horizontal) orientation, end cap 630 of support body 610 should be higher than the opposing end of support body 610. This promotes movement of bubbles toward relief ports 646/648 and prevents bubbles from accumulating inside fluid conduit 634. The configuration of fluid conduit 634 promotes rapid clearing of bubbles from fluid conduit 634 while reducing turbulent flow of the couplant, which might otherwise cause bubbles to remain in the couplant located between arrays 614/616 and structure 702. For instance, fluid conduit 634 may utilize rounded or chamfered edges, tapered sides, and/or exit ports sized to prevent back pressure—these features contribute to the reduction of turbulence. In particular, fluid conduit 634 directs the couplant across the major longitudinal faces of ultrasonic transducer arrays 614/616 in a manner that eliminates accumulation of gas bubbles on arrays 614/616. In certain embodiments, bubbles can be cleared in less than three seconds when a flow rate of about one gallon per minute is maintained. Clearing bubbles from fluid conduit 634 reduces errors in the collected test data.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An apparatus for non-destructive inspection of a structure, comprising:
    a support body;
    a first ultrasonic transducer array coupled to a first portion of the support body and configured to inspect the structure at a first frequency as the support body is moved over the structure;
    a second ultrasonic transducer array coupled to a second portion of the support body and configured to inspect the structure at a second frequency as the support body is moved over the structure; and
    a fluid conduit formed within the support body and configured to simultaneously disperse a couplant between a first longitudinal flow channel corresponding to the first ultrasonic transducer array and a second longitudinal flow channel corresponding to the second ultrasonic transducer array, wherein the first longitudinal flow channel and the second longitudinal flow channel are parallel and non-colinear, and wherein a fluid inlet is located between the first longitudinal flow channel and the second longitudinal flow channel.

2. The apparatus of claim 1, the fluid conduit being further configured to simultaneously disperse the couplant between the first ultrasonic transducer array and a surface under test, and the second ultrasonic transducer array and the surface under test.

3. The apparatus of claim 1, further comprising:
    the first ultrasonic transducer array and the second ultrasonic transducer array being configured to simultaneously inspect the structure as the support body is moved over the structure; and
    the first ultrasonic transducer array being configured to inspect the structure for relatively low porosity using a relatively high frequency, and the second ultrasonic transducer array being configured to inspect the structure for relatively high porosity using a relatively low frequency.

4. The apparatus of claim 1, further comprising a frame coupled to the support body, the frame comprising an attachment feature for a motion control device that moves the apparatus over the structure for inspection in a direction perpendicular to the major longitudinal axis of the first and second ultrasonic transducer arrays, wherein the major longitudinal axis of the first and second ultrasonic transducer arrays are parallel.

5. The apparatus of claim 1, the support body comprising a base having formed therein a first opening corresponding to the first ultrasonic transducer array and a second opening corresponding to the second ultrasonic transducer array, the support body being configured to hold transducers in the first ultrasonic transducer array away from the first opening and to hold transducers in the second ultrasonic transducer array away from the second opening.

6. The apparatus of claim 5, the fluid conduit being defined at least in part by space between transducers in the first ultrasonic transducer array and the first opening, and space between transducers in the second ultrasonic transducer array and the second opening.

7. The apparatus of claim 1, further comprising:
    the support body comprising:
        a frame configured for supporting the first ultrasonic transducer array and the second ultrasonic transducer array; and
    at least one sled appendage configured for supporting the frame while traveling over a surface of the structure and rotatably connected to the frame; and
    a braking system capable of affixing the respective positions of the frame and sled appendage in at least a first direction of motion about a first axis defined by the rotatable connection of the frame and the sled appendages.

8. An apparatus for non-destructive inspection of a structure, comprising:
    a support body having formed therein a fluid inlet and a fluid conduit in communication with the fluid inlet; and
    a first ultrasonic transducer array coupled to a first portion of the support body and configured to inspect the structure as the support body is moved over the structure, the first ultrasonic transducer array comprising a first end, a second end, and a plurality of first transducers arranged between the first end and the second end;
    a second ultrasonic transducer array coupled to a second portion of the support body and configured to inspect the structure as the support body is moved over the structure, the second ultrasonic transducer array comprising a third end, a fourth end, and a plurality of second transducers arranged between the third end and the fourth end; and
    the fluid inlet being located between a first longitudinal flow channel corresponding to the first ultrasonic transducer array and a second longitudinal flow channel corresponding to the second ultrasonic transducer array, wherein the first longitudinal flow channel and the second longitudinal flow channel are parallel and non-colinear;

the fluid conduit being configured to disperse the couplant between the first longitudinal flow channel and the second longitudinal flow channel, wherein the couplant flows down the first longitudinal flow channel from a location proximate the first end of the first ultrasonic transducer array to a location proximate the second end of the first ultrasonic transducer array, and wherein the couplant flows down the second longitudinal flow channel from a location proximate the third end of the second ultrasonic transducer array to a location proximate the fourth end of the second ultrasonic transducer array.

9. The apparatus of claim 8, wherein:
the support body comprises a base having formed therein a first opening for ultrasonic energy generated by the first ultrasonic transducer array and a second opening for ultrasonic energy generated by the second ultrasonic transducer array;
the first longitudinal flow channel comprising chamfered sidewalls between the first end of the first ultrasonic transducer array and the second end of the first ultrasonic transducer array, the chamfered sidewalls terminating at the first opening; and
the second longitudinal flow channel comprising chamfered sidewalls between the third end of the second ultrasonic transducer array and the fourth end of the second ultrasonic transducer array, the chamfered sidewalls terminating at the second opening.

10. The apparatus of claim 8, wherein the first and second longitudinal flow channels terminate at a corresponding first and second relief port that is sized to restrict fluid flow relative to the first and second longitudinal flow channel.

11. The apparatus of claim 10, the corresponding first and second relief port being configured to accommodate ejection of at least some of the couplant, and gas bubbles contained therein, from the first and second longitudinal flow channel.

12. The apparatus of claim 8, the support body comprising:
a base having formed therein an opening for ultrasonic energy generated by the ultrasonic transducer array; and
a registration element configured to hold the ultrasonic transducer array away from the opening such that the ultrasonic transducer array defines at least a portion of the fluid conduit and such that the couplant fills a space between the ultrasonic transducer array and the opening.

13. The apparatus of claim 8, further comprising:
the support body comprising:
a frame configured for supporting the first ultrasonic transducer array and the second ultrasonic transducer array; and
at least one sled appendage configured for supporting the frame while traveling over a surface of the structure and rotatably connected to the frame; and
a braking system capable of affixing the respective positions of the frame and sled appendage in at least a first direction of motion about a first axis defined by the rotatable connection of the frame and the sled appendages.

14. A system for inspecting a structure, comprising:
a motion control system;
a probe coupled to and moved by the motion control system over the structure in a direction perpendicular to the major longitudinal axis of a plurality of ultrasonic transducer arrays, the probe comprising:
a support body having formed therein a fluid inlet and a fluid conduit in communication with the fluid inlet;
the plurality of ultrasonic transducer arrays held by the support body and configured to simultaneously inspect the structure using a plurality of frequencies as the probe is moved over the structure; and
the fluid conduit configured to simultaneously disperse a couplant between at least two longitudinal flow channels, each longitudinal flow channel corresponding to an ultrasonic transducer array in the plurality of ultrasonic transducer arrays; and
data collection equipment coupled to the plurality of ultrasonic transducer arrays and configured to simultaneously receive, from the plurality of ultrasonic transducer arrays, test signals corresponding to the plurality of frequencies.

15. The system of claim 14, the support body comprising a base having formed therein a plurality of openings corresponding to the plurality of ultrasonic transducer arrays, the support body being configured to hold transducers in the plurality of ultrasonic transducer arrays away from the plurality of openings.

16. The system of claim 14, further comprising:
a fluid delivery subsystem coupled to the fluid inlet and configured to deliver the couplant to the probe under a pressure and a flow rate, wherein the fluid delivery subsystem is configured to deliver the couplant at the flow rate of three gallons per minute.

17. The system of claim 14, wherein:
the plurality of ultrasonic transducer arrays comprises a high frequency ultrasonic transducer away and a low frequency ultrasonic transducer array, and
the data collection equipment is configured to independently receive a first set of test signals from the high frequency ultrasonic transducer array and a second set of test signals from the low frequency ultrasonic transducer array.

18. The system of claim 14, the probe further comprising at least one relief port for the fluid conduit, the at least one relief port being configured to accommodate ejection of at least some of the couplant, and gas bubbles contained therein, from the fluid conduit.

19. The system of claim 14, further comprising:
the support body comprising:
a frame configured for supporting the plurality of ultrasonic transducer arrays; and
at least one sled appendage configured for supporting the frame while traveling over a surface of the structure and rotatably connected to the frame; and
a braking system capable of affixing the respective positions of the frame and sled appendage in at least a first direction of motion about a first axis defined by the rotatable connection of the frame and the sled appendages.

20. A method for inspecting a structure, the method comprising:
holding a probe against a surface of the structure, the probe comprising a high frequency ultrasonic transducer array, a low frequency ultrasonic transducer array, and a fluid conduit configured to simultaneously disperse a couplant between a first longitudinal flow channel corresponding to the high frequency ultrasonic transducer array and a second longitudinal flow channel corresponding to the low frequency ultrasonic transducer array, wherein the first longitudinal flow channel and the second longitudinal flow channel are parallel and non-colinear;
simultaneously transmitting high frequency ultrasonic test signals to the high frequency ultrasonic transducer array and low frequency ultrasonic test signals to the low frequency ultrasonic transducer array;

coupling ultrasonic signals between the high frequency ultrasonic transducer array and the structure using the couplant;
coupling ultrasonic signals between the low frequency ultrasonic transducer array and the structure using the couplant;
moving the probe across the surface of the structure; and
processing a first set of detection signals from the high frequency ultrasonic transducer array and a second set of detection signals from the low frequency ultrasonic transducer array, the first set of detection signals being generated in response to transmitted high frequency ultrasonic signals, and the second set of detection signals being generated in response to transmitted low frequency ultrasonic signals.

21. The method of claim 20, wherein the probe further comprises:
a frame for supporting the high frequency ultrasonic transducer array, the low frequency ultrasonic transducer array, and the fluid conduit;
at least one sled appendage rotatably connected to the frame and for contacting the surface; and
an axial braking system for fixing the position of the sled appendage and in communication with a motion control system connected to the probe.

* * * * *